United States Patent [19]

Savolskis et al.

[11] 4,338,117

[45] Jul. 6, 1982

[54] ATMOSPHERE SENSING DEVICE FOR A FURNACE

[75] Inventors: Edward P. Savolskis, Carlisle; Terrence L. Sanders, Boiling Springs, both of Pa.

[73] Assignee: PPG Industries, Inc., Pittsburgh, Pa.

[21] Appl. No.: 227,015

[22] Filed: Jan. 21, 1981

[51] Int. Cl.³ .................................................. C03B 5/24
[52] U.S. Cl. ........................................ 65/158; 65/162; 65/182.4; 65/355; 65/356
[58] Field of Search ................ 65/158, 162, 355, 356, 65/DIG. 13, 182.4; 73/23

[56] References Cited

U.S. PATENT DOCUMENTS 3,218,842 11/1965 Ludwig et al. .......................... 73/23
3,515,529 6/1970 Love et al. ........................ 65/356 X
3,759,087 9/1973 Iwao et al. .............................. 73/23
3,954,433 5/1976 Holler ........................... 65/DIG. 13

OTHER PUBLICATIONS

*Glass Furnace Oxygen Sensors and Monitors* by Corning Glass Works, Ceramic Products Division, Corning, New York.

*Primary Examiner*—Arthur D. Kellogg
*Attorney, Agent, or Firm*—Donald Carl Lepiane

[57] ABSTRACT

A device for sensing the oxygen content in exhaust gases in a regenerative furnace for evaluating combustion efficiency includes an oxygen probe and conduit cast in a ceramic block. Water moved through the conduit provides structural stability to the ceramic block and protects the probe against thermal damage.

8 Claims, 8 Drawing Figures

ATMOSPHERE SENSING DEVICE FOR A FURNACE

BACKGROUND OF THE INVENTION

1. Field of the Invention

This invention relates to a device for sensing the atmosphere in a regenerative furnace or regenerator such as the type used for a glass making apparatus.

2. Discussion of the Technical Problems

Regenerators of glass making apparatuses, e.g. flat glass making apparatuses, usually include a gas pervious bed of refractory material, such as a stacked arrangement of bricks, sometimes called "checker packing", through which hot exhaust gases are passed during one heating cycle in order to heat the packing. In alternate heating cycles, the flow is reversed and the heat stored in the packing serves to preheat combustion air passing through the regenerator. The regenerators are usually employed in pairs, with one on either side of the combustion chamber. While one regenerator is absorbing heat from the exhaust gas, the other is heating incoming air.

A sensing probe may be mounted in the regenerators above the checker packing to monitor percent of oxygen in the exhaust gas for subsequent control of oxygen content in the combustion chamber and to evaluate combustion efficiency. For example, if the percent of oxygen in the chamber atmosphere is above a predetermined level, the excess oxygen may upset the chemical balance in the combustion chamber. If the percent of oxygen in the chamber atmosphere is below a predetermined level, the combustion in the chamber may be incomplete.

Continuous oxygen sensing probes presently available have a short usable life because of thermal breakage and/or damage when exposed to the temperatures, e.g. between 2300° F. (1260° C.) and 3100° F. (1704° C.) in the combustion chamber and/or regenerators. It would be advantageous, therefore, to provide thermal protection for continuous oxygen sensing probes used in regenerators such as regenerators of flat glass making apparatuses to increase the usable life of the devices.

SUMMARY OF THE INVENTION

This invention relates to an improved sensing device for monitoring gas content of a heated atmosphere, e.g. in the temperature range of about 1112° F. (600° C.)-3050° F. (1676° C.) in a furnace, e.g. oxygen content of exhaust gases passing through a regenerator of a glass making apparatus. The device includes an oxygen sensing probe mounted in a ceramic block and a water-cooled block support. The water-cooled support reduces thermal shock to the probe during installation and thermal damage to the probe after installation to increase the usable life of the probe. The support also provides structural stability to the ceramic block, by eliminating the effect of cantilever forces acting on the suspended ceramic block to allow deeper insertion of the probe into the regenerator or furnace interior for a more representative monitoring of the exhaust gases passing through the regenerator or of the furnace atmosphere respectively.

DESCRIPTION OF THE INVENTION

Figure 1:
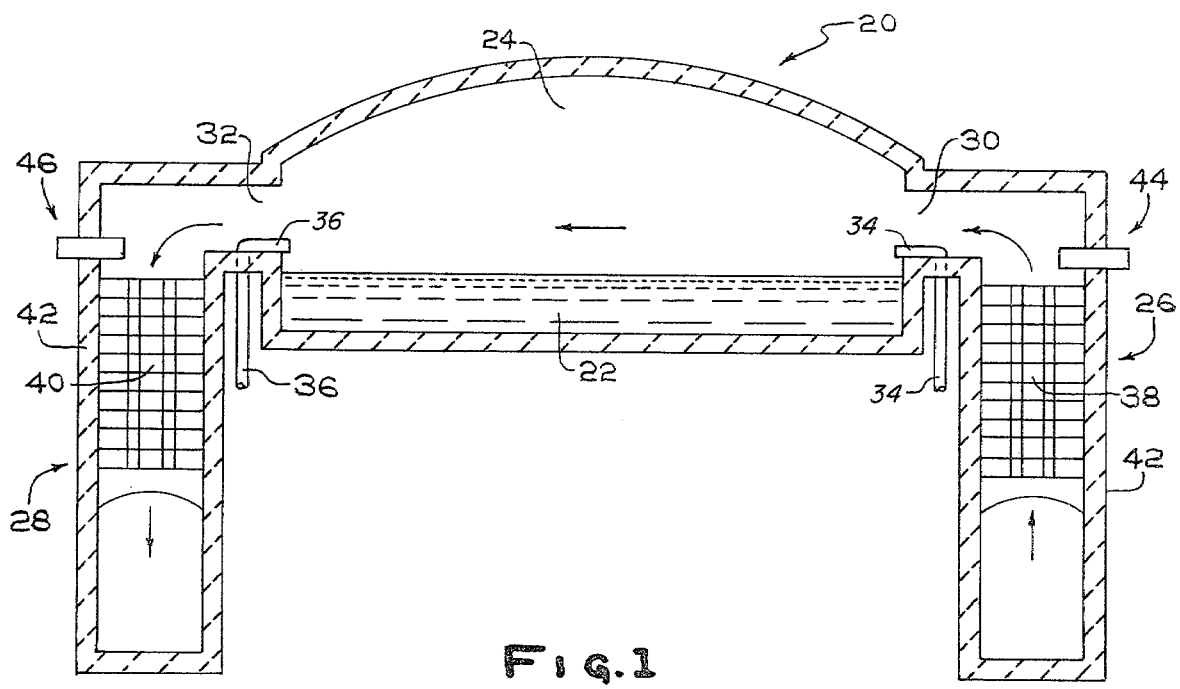
FIG. 1 is a schematic, vertical section across the width of a cross-fired, regenerative, glass-melting furnace having a sensing device of the instant invention mounted in each regenerator.

The regenerative furnace arrangement 20, shown in FIG. 1, is typical of the melting furnaces used in the flat glass industry. It should be understood that such a furnace is being described as an illustrative example and that the invention is applicable to regenerative furnaces, recuperators, regenerators of other types and/or other furnaces. As shown in FIG. 1, a pool of molten impartially melted glass 22 is contained in melting zone 24 which also serves as a combustion chamber. Regenerators 26 and 28 flank the combustion chamber 24 and communicate therewith by a plurality of burner ports 30 and 32 respectfully. Fuel for combustion is supplied by pipes 34 or 36. Air for combustion passes upwardly through a regenerator 26 or 28 where it is preheated by passing over a hot gas pervious refractory brick work checker packing bed 38 or 40 and then through port 30 or 32 where it combines with fuel from the pipe 34 or 36, respectively, at the mouth of the port. Flames issue a considerable distance into the combustion chamber 24 and hot exhaust gases through the port 32 or 30 and into the opposite regenerator 28 or 26 where the exhaust gases heat the refractory packing bed 40 or 38 respectively. The mode of operation, as shown in FIG. 1, is an intake or firing cycle with respect to the regenerator 26 and an exhaust cycle with respect to the regenerator 28. After several minutes of operation, the flows are reversed so that the refractory packing bed 40 of the regenerator 28 serves to preheat combustion air and flames issue from left to right from the port 32 toward the port 30. The regenerator 26 would then be in an exhaust cycle. After several minutes, the direction of flows are again reversed to that shown in FIG. 1 and so on. A complete discussion of a regenerative furnace of a flat glass making apparatus is found in U.S. Pat. No. 4,047,560 which teachings are hereby incorporated by reference.

Mounted in wall 42 of each regenerator 26 and 28 and extending over a portion of the packing 38 and 40 is an atmosphere sensing device 44 and 46 respectively incorporating features of the invention for monitoring quantitatively presence of a selected gas or gases in the exhaust atmosphere or gases. For example, the sensing device 44 of the regenerator 26 monitors the oxygen content in the incoming exhaust gases resulting from the combustion occurring at the burner port 32, and the sensing device 46 of the regenerator 28 monitors the oxygen content in the incoming exhaust gases from the combustion occurring at the burner port 30.

In the following discussion, reference is made to the device 46 with the understanding that the discussion is applicable to the device 44 unless indicated otherwise.

Figure 2:
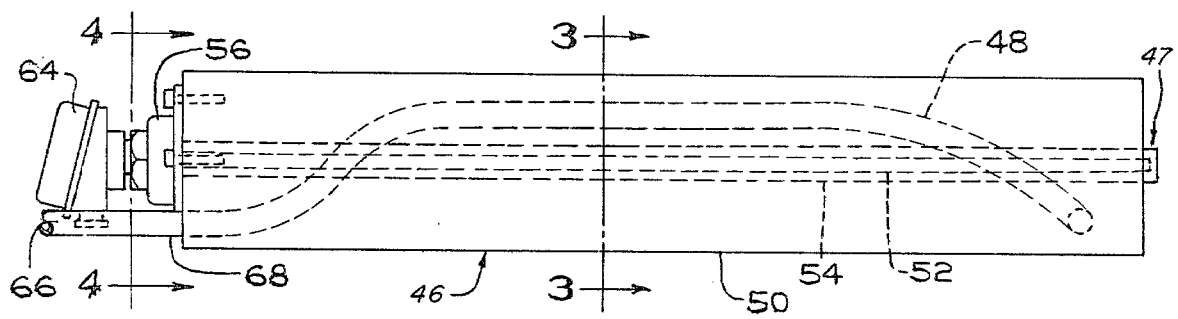
FIG. 2 is a side elevated view of a sensing device incorporating features of the instant invention.
Figure 3:
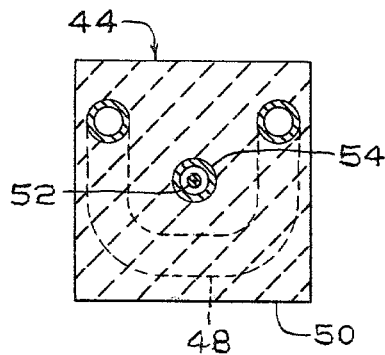
FIG. 3 is a view taken along lines 3—3 of FIG. 2.
Figure 4:
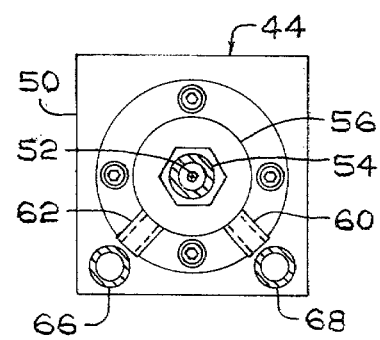
FIG. 4 is a view taken along lines 4—4 of FIG. 2.

Referring to FIGS. 2–4, the device 46 includes an oxygen sensing probe 47 and cooling support or conduit 48 conveniently mounted in a refractory block 50. The probe 47 is not limiting to the invention and may be any of the types used in the art for monitoring or analyzing an atmosphere in a regenerator or furnace interior. A probe 47 used in the practice of the invention includes a Corning Oxygen Sensor 52 Model No. 8081-5 in a protection tube 54, e.g. an alumina or Zirconia protection tube; a Corning water cooled probe head 56 Model No. D-8061 having inlet tube 60 and outlet tube 62 (clearly shown in FIG. 4); and a connector heat 64 for external electrical access to the sensor 52 for monitoring sensor output signal to determine oxygen content in the exhaust gases.

The support or conduit 48 in the ceramic block 50 provides structural stability to the block 50 to counteract cantilever forces acting on the block 50 when mounted over the packing 38 or 40 in the regenerators 26 and 28 respectively. These cantilever forces, if not minimized or eliminated, can cause shearing of the block. Further, by minimizing or eliminating these cantilever forces, the probe 47 can be further inserted into the flow of the exhaust gases for a more accurate determination of oxygen content in the exhaust gases. The support or conduit 48 also provides for moving a cooling medium, e.g. water through the block 50 to prevent thermal damage to the probe after installation to increase the usable life of the probe. The conduit 48 prevents thermal damage by depressing the overall temperature of the probe. For example, when the interior temperature of the regenerator is about 2912° F. (1600° C.), the probe used in accordance with the teachings of the instant invention has a temperature of about 2822° F. (1550° C.) with a peak temperature of about 2876° F. (1580° C.). By depressing the temperature of the probe, the usable life of the probe is increased and deeper insertion of the probe into the regenerator interior can be obtained. The mass of the ceramic block prevents or eliminates thermal shock to the probe 47 during insertion and after installation e.g. during the reversal of the firing cycle. Further, the coating fluid e.g. water passing through the conduit 48 cools the ceramic block. Although not limiting to the invention, a support or conduit 48 used in the practice of the invention is made of black iron or stainless steel.

The conduit 48 may be mounted in the block in any configuration to accomplish at least the above. Shown in FIGS. 2–4 is a conduit configuration used in the practice of the invention. As shown in FIGS. 2 and 4, inlet end 66 and outlet end 68 of the conduit 48 are at the bottom portion of the block end as mounted in the regenerator wall. The path of the conduit 48 is curved upward as shown in FIG. 2 and extends toward the right end of the block 50. Adjacent the right end of the block 52, as shown in FIG. 2, the conduit curves downward (see also FIG. 3). The probe 47 as shown in FIGS. 2 and 3 is spaced from and between the conduit 48. The flow of the water through the conduit is not limiting to the invention. For example, water moving through a conduit made of about ½ inch (1.27 centimeters) stainless steel pipe having a wall thickness of about 0.109 inch (0.277 centimeters) at a flow rate of about 10 gallons per minute (63.1 meter 3 per second) was used with a ceramic block having a length of about 35-½ inches (0.89 meters) and a square cross sectional configuration of about 5 inches (12.70 centimeters). The device 46 having the probe 47 and conduit 48 in a ceramic block 50 was mounted in a regenerator of a flat glass making apparatus and exposed to temperatures of up to about 3050° F. (1676° C.). The probe 47 monitored oxygen content in the exhaust gases of the regenerator for over five months, which is about twice the expected life of a probe not mounted in a ceramic block according to the teachings of the invention.

The block 50 may be made of any refractory material known in the art that is capable of withstanding the hostile atmosphere in the regenerator. In the practice of the invention, the probe 47 and conduit 48 described above were cast in a Purotab ® castable alumina refractory to provide the ceramic block having the above mentioned dimensions. Although not limiting to the invention, it is preferred that the end of the probe 47 extend beyond the adjacent block end about ½ inch (1.27 centimeters) for direct exposure to the exhaust gases.

Figure 5:
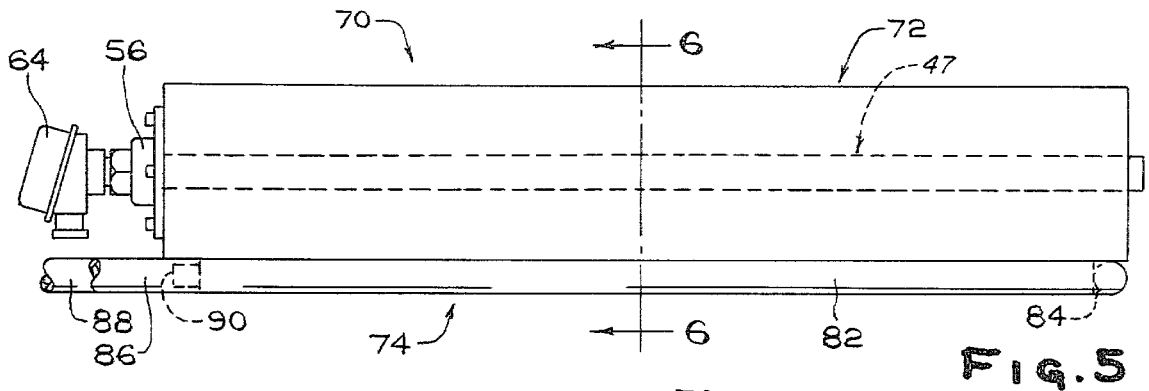
FIG. 5 is a side elevated view of another embodiment of a sensing probe incorporating features of the invention.
Figure 6:
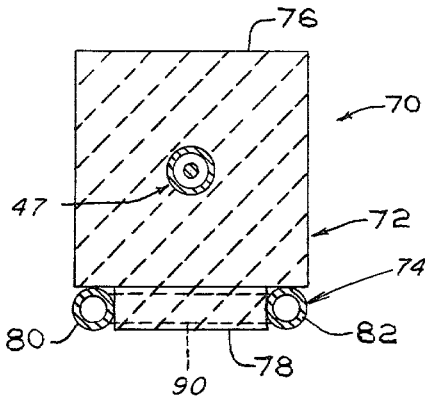
FIG. 6 is a view taken along lines 6—6 of FIG. 5.
Figure 7:
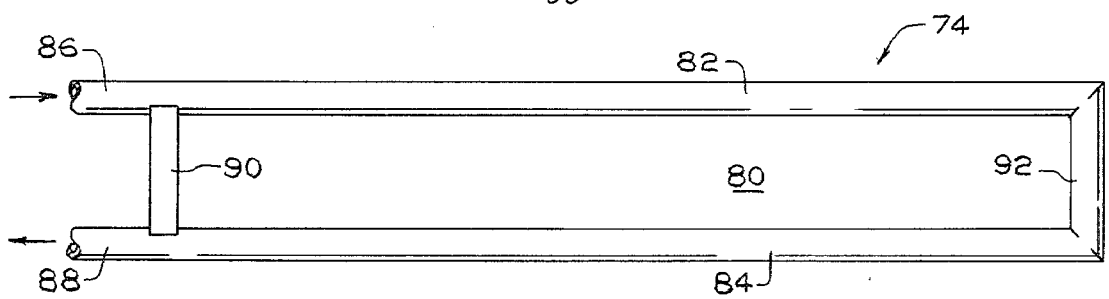
FIG. 7 is a top elevated view of the block support of the sensing probe shown in FIG. 5.
Figure 8:
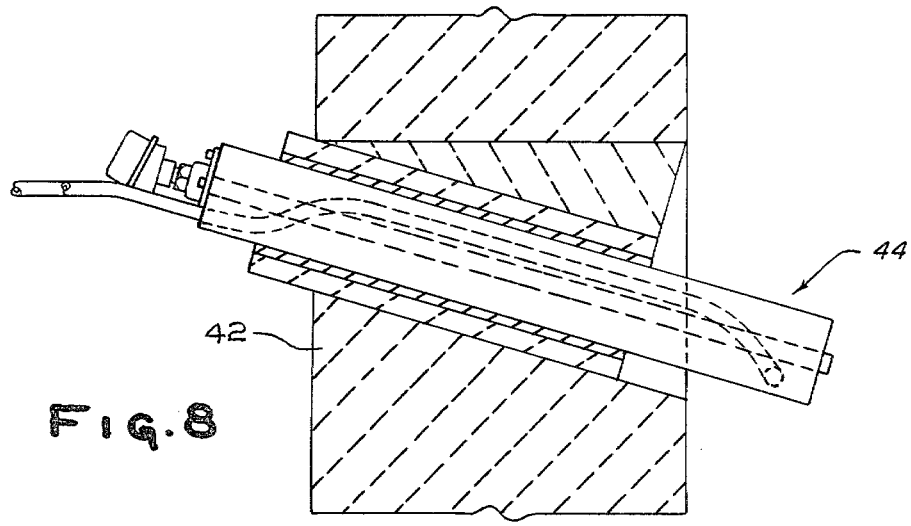
FIG. 8 is a side elevated sectional view illustrating an embodiment for mounting the sensing device of the instant invention in a regenerator wall.

Shown in FIGS. 5–7 in another embodiment of the invention. Device 70 includes a ceramic block 72 having the probe 47 and a cooling support 74 clearly shown in FIG. 7. With reference to FIG. 6, the ceramic block 72 includes a body portion 76 containing the probe 47 and an extension 78 insertable in groove 80 of the support 74. With specific reference to FIG. 7, the support 74 includes a pair of pipes 82 and 84 spaced at inlet end 86 and outlet end 88 respectively by a strap 90 and spaced and interconnected at their other end by intermediate pipe 92. The device 44 of FIGS. 2–4 or 70 of FIGS. 5–7 is mounted in the regenerator wall 42 in any convenient manner and in any position. For example, the device may be horizontally mounted as shown in FIG. 1 or at an angle, e.g. about a 10° angle to the horizontal as shown in FIG. 8. Although not limiting to the invention, the device 44 or 70 may be mounted in peep holes extended over the packing bed or in flues below the packing bed and secured in position by a refractory cement.

As can now be appreciated, the invention is not limited to the above examples which were presented for illustration purposes only. More particularly, the type of probe used in the practice of the invention can be any of the types used to analyze or monitor a particular gas in a furnace or a regenerative furnace. Further, the refractory material selected should be capable of withstanding the temperature and atmosphere within the regenerative furnace.

What is claimed is:

1. In a device for sensing atmosphere in a furnace, wherein the device is mounted in a furnace wall and extends beyond the interior surface of the furnace wall, the device is of the type having a ceramic block made of a material substantially non-reactive with the furnace atmosphere; and a probe for sensing the furnace atmosphere, the probe mounted in the block to minimize thermal shock to the probe, the improvement comprising:

conduit means adjacent a substantial length of the probe, said conduit means having inlet and outlet ends accessible from the block exterior for moving a cooling medium through said conduit means to minimize thermal shock and thermal damage to the probe and said conduit means formed of a metal or metal alloy having a wall thickness sufficient to provide substantially rigid support to the ceramic block.

2. The device as set forth in claim 1 wherein the furnace is a glass melting furnace having a regenerator and exhaust gases passing through the regenerator are monitored.

3. The device as set forth in claim 2 wherein the oxygen content in the exhaust gases is monitored and the probe is an oxygen sensing probe.

4. The device as set forth in claim 1, 2 or 3 wherein said conduit means is in the block.

5. The device as set forth in claim 4 wherein the block is made of a refractory material and the probe and said conduit means are cast in the block.

6. The device as set forth in claim 1, 2 or 3 wherein the probe is in the block and said conduit means is a support exterior of the block.

7. The device as set forth in claim 6 wherein the block is made of a refractory material and the probe is cast in the block.

8. The device as set forth in claim 7 wherein the block has an extension and said conduit means is shaped for receiving the extension.

* * * * *